United States Patent
Seto et al.

(10) Patent No.: US 6,232,469 B1
(45) Date of Patent: May 15, 2001

(54) 4-ACYLAMINO-2,2,6,6-TETRAMETHYLPIPERIDINE DERIVATIVES AND ANTIOXIDANTS CONTAINING THE SAME

(75) Inventors: Nobuo Seto; Takayoshi Kamio, both of Minami Ashigara (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 09/400,301

(22) Filed: Sep. 21, 1999

(30) Foreign Application Priority Data

Sep. 21, 1998 (JP) .................................. 10-266696

(51) Int. Cl.⁷ ......................... C07D 211/58; C09K 15/30
(52) U.S. Cl. ......................... 546/244; 252/405; 252/399; 252/397; 430/202; 430/235
(58) Field of Search ............................ 546/244; 252/405, 252/399, 397; 106/20 D; 347/1; 430/202, 235, 237

(56) References Cited

PUBLICATIONS

Kornberg, R. D. et al.: Measurement of transmembrane potentials in phospholipid vesicles. Proc. Nat. Acad. Sci. vol. 69, pp. 1508–1513, 1972.*

Greenspoon, N. et al.: reverse micelles as a model system for carbohydrate binding. J. Am. Chem. Soc. vol. 113, pp. 1233–1236, 1991.*

* cited by examiner

Primary Examiner—C. S. Aulakh
(74) Attorney, Agent, or Firm—Birch, Stewart, Kolasch & Birch LLP

(57) ABSTRACT

A novel 4-acylamino-2,2,6,6-tetramethylpiperidine derivatives and antioxidants comprising the same.

The 4-acylamino-2,2,6,6-tetramethylpiperidine derivatives are represented by formula (A):

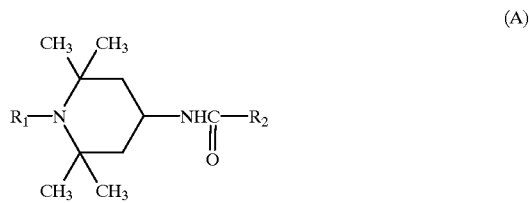

wherein $R_1$ represents a hydrogen atom, a hydroxyl group, an oxyradical group, an aliphatic group, an acyl group, an aliphatic oxy group or an acyloxy group; and $R_2$ represents an aliphatic group having at least 3 carbon atoms and at least two hydroxyl groups.

18 Claims, No Drawings

4-ACYLAMINO-2,2,6,6-TETRAMETHYLPIPERIDINE DERIVATIVES AND ANTIOXIDANTS CONTAINING THE SAME

FIELD OF THE INVENTION

This invention relates to novel 4-acylamino-2,2,6,6-tetramethylpiperidine derivatives. More particularly, it relates novel 4-acylamino-2,2,6,6-tetramethylpiperidine derivatives which are useful as antioxidants and antioxidants containing the same.

BACKGROUND OF THE INVENTION

It is widely known that dyes (e.g., azo dyes, azomethine dyes and anthraquinone dyes), colorants or polymers (for example, rubbers and plastics) are deteriorated by oxidative reactions in which oxygen in air participates. Accordingly, there have been developed various deterioration inhibitors typified by various antioxidant compounds such as phenols and hydroquinones as disclosed, e.g., in JP-A-59-87456, JP-A-59-180557 and JP-A-59-189342 (the term "JP-A" as used herein means an "unexamined published Japanese patent application").

However, none of these conventional deterioration inhibitors is satisfactory in the performance of preventing colorants, dyes, synthetic polymers, etc. from deterioration. Thus, it has been required to develop novel antioxidants.

SUMMARY OF THE INVENTION

An object of the present invention is to provide novel 4-acylamino-2,2,6,6-tetramethylpiperidine derivatives as antioxidants.

Another object of the present invention is to provide antioxidants containing novel 4-acylamino-2,2,6,6-tetramethylpiperidine derivatives.

A further object of the present invention is to provide novel 4-acylamino-2,2,6,6-tetramethyipiperidine derivatives which are useful as antioxidants for polymers.

The present inventors have conducted intensive studies. As a result, they have developed 4-acylamino-2,2,6,6-tetramethylpiperidine derivatives represented by the following formula (A) and found out that these derivatives exhibit excellent antioxidant effects:

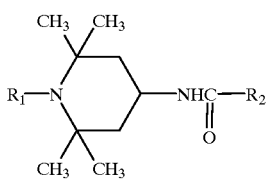

(A)

wherein $R_1$ represents a hydrogen atom, a hydroxyl group, an oxyradical group, an aliphatic group, an acyl group, an aliphatic oxy group or an acyloxy group; and $R_2$ represents an aliphatic group having at least 3 carbon atoms and at least two hydroxyl groups.

DETAILED DESCRIPTION OF THE INVENTION

Now, the formula (A) will be illustrated in greater detail.

When a group given herein contains an aliphatic moiety, the aliphatic moiety may be either a linear, branched or cyclic one. Also, it may be either a saturated or unsaturated one. Examples thereof include alkyl, alkenyl, cycloalkyl and cycloalkenyl groups which may have substituent(s). When a group given herein contains an aryl moiety, the aryl moiety may be either a monocyclic or fused ring one which may have substituent(s). When a group given herein contains a heterocyclic moiety, the heterocyclic moiety has heteroatom(s) (for example, nitrogen, sulfur or oxygen atoms) in its cycle. It is either a saturated or unsaturated one. Also, it is either a monocyclic or fused ring one which may have substituent(s).

The term "substituent" as used herein means any substitutable group exemplified by aliphatic, aryl, heterocyclic, acyl, acyloxy, acylamino, aliphaticoxy, aryloxy, heterocyclic oxy, aliphatic oxycarbonyl, aryloxycarbonyl, heterocyclic oxycarbonyl, carbamoyl, aliphatic sulfonyl, arylsulfonyl, heterocyclic sulfonyl, aliphatic sulfonyloxy, arylsulfonyloxy, heterocyclic sulfonyloxy, sulfamoyl, aliphatic sulfonamido, arylsufonamido, heterocyclic sulfonamido, aliphatic amino, arylamino, heterocyclic amino, aliphatic oxycarbonylamino, aryloxycarbonylamino, heterocyclic oxycarbonylamino, aliphatic sulfinyl, arylsulfinyl, aliphatic thio, arylthio, hydroxyl, cyano, sulfo, carboxyl, aliphatic oxyamino, aryloxyamino, carbamoylamino, sulfamoylamino, sulfamoylcarbamoyl, carbamoylsulfamoyl, dialiphatic oxyphosphonyl and diaryloxyphosphonyl groups and halogen atoms.

$R_1$, represents a hydrogen atom, a hydroxyl group, an oxyradical group, an aliphatic group (for example, optionally substituted alkyl or alkenyl, preferably alkyl and still preferably alkyl having 1 to 8 carbon atoms such as methyl, ethyl, propyl or octyl), an acyl group (for example, optionally substituted alkylcarbonylamino, alkenylcarbonylamino or arylcarbonylamino, preferably alkylcarbonylamino and still preferably alkylcarbonylamino having 1 to 7 carbon atoms in the alkyl moiety such as acetyl, propionyl orbutyryl), analiphatic oxy group (for example, optionally substituted alkoxy or alkenoxy, preferably alkoxy and still preferably alkoxy having 1 to 8 carbon atoms such as methoxy, ethoxy, propoxy or octyloxy) or an acyloxy group (for example, optionally substituted alkylcarbonyloxy, alkenylcarbonyloxy or arylcarbonyloxy, preferably alkylcarbonyloxy and still preferably alkylcarbonyloxy having 1 to 7 carbon atoms in the alkyl moiety such as acetoxy or propionyloxy). $R_2$ represents an aliphatic group having at least 3 carbon atoms and at least two hydroxyl groups (alkyl or alkenyl optionally having substituent(s) other than the hydroxyl groups, preferably alkyl and still preferably alkyl having 3 to 7 carbon atoms and 2 to 6 hydroxyl groups such as 1,3-dihdyroxy-2,2-ddmethylpropyl or 1,2,3,4,5-pentahydroxypentyl).

From the viewpoint of the effects of the present invention, it is preferable that $R_1$ is a hydrogen atom, a hydroxyl group, an oxyradical group or an alkyl group, still preferably a hydrogen atom or an oxyradical group and a hydrogen atom in the most desirable case.

Next, particular examples of the compounds of the present invention will be illustrated, though the present invention is not restricted thereto.

(1)

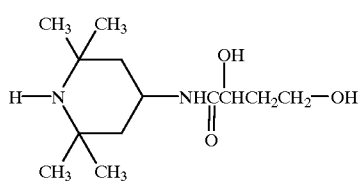

(lactone employed as starting material:
(±)-α-hydroxy-γ-butyrolacotne)

(2)

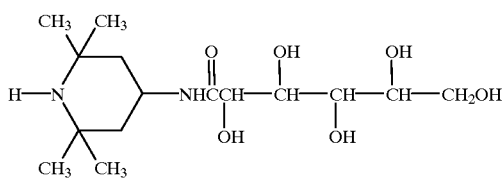

(lactone employed as starting material:
D-(+)-glucono-1,5-lacotne)

(3)

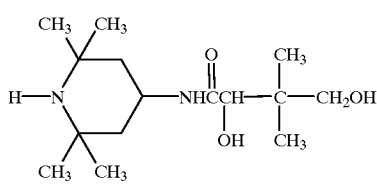

(lactone employed as starting material:
DL-pantoyllacotne)

(4)

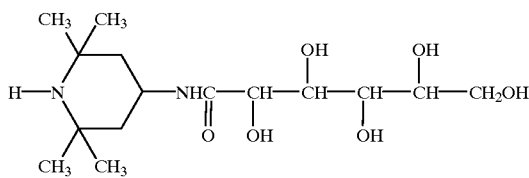

(lactone employed as starting material:
γ-D-galactonolacotne)

(5)

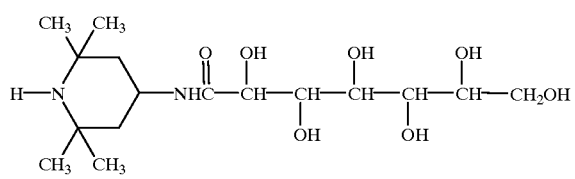

(lactone employed as starting material:
α-D-glucoheptonic-γ-lactone)

(6)

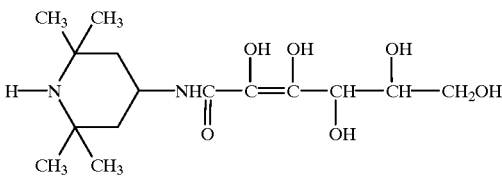

(lactone employed as starting material:
L-ascorbic acid)

(7)

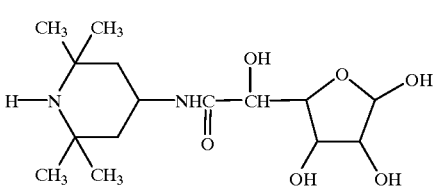

(lactone employed as starting material:
D-glucurono-6,3-lacotne)

(8)

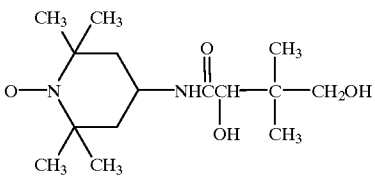

(lactone employed as starting material:
DL-pantoyllactone)

(9)

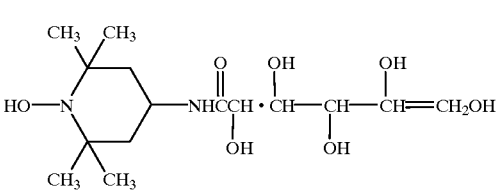

(lactone employed as starting material:
D-(+)-glucono-1,5-lacotne)

(10)

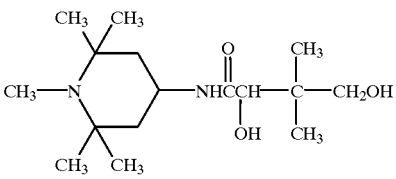

(lactone employed as starting material:
    DL-pantoyllactone)

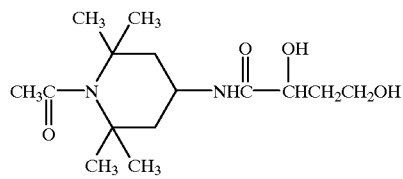
(11)

(lactone employed as starting material:
    (±)-α-hydroxy-γ-butyrolacotne)

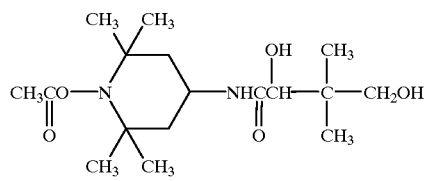
(12)

(lactone employed as starting material:
    DL-pantoyllacotne)

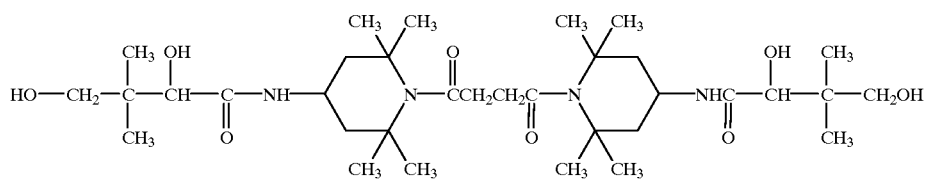
(13)

(lactone employed as starting material:
    DL-pantoyllacotne).

As the 2,2,6,6-tetramethylpiperidine skeleton of the compounds represented by the formula (A) according to the present invention, 4-amino-2,2,6,6-tetramethylpiperidine, 4-amino-2,2,6,6,-tetramethylpiperidin-1-oxyl free radical, etc. are marketed and easily obtained. The compounds of the formula (A) can be synthesized by various reactions such as amidation, alkylation, oxidation, reduction, etc. using these starting materials. As a general method for introducing the group $R_2$ in the formula (A), it is convenient and preferable to perform amidation by reacting an amine compound and a lactone compound by reference to the method described in "Shin Jikken Kagaku Koza (New Studies on Experimental Chemistry) ", vol. 14, p. 1150 (1977), MARUZEN Co., Ltd. As the starting lactone compound, D-(+)-glucono-1,5-lactone, DL-pantoyllactone, etc. can be easily obtained. More particularly speaking, an amino compound and a lactone compound are reacted in an alcoholic solvent or a sulfolane solvent at room temperature to under reflux. As an alkylation reaction for introducing the group $R_1$ in the formula (A), it is preferable to reflux formalin or to react an alkyl halide with potassium carbonate in dimethylformamide at about 100° C. Moreover, the acylation is preferably exemplified by a reaction with an acid anhydride or an oxyl free radical reaction; the hydroxylation is preferably exemplified by a method in accordance with Helv. Chem. Acta (1980)63, 1407 with the use of hydrogen peroxide; the alkoxylation is preferably exemplified by a reaction between an alkyl halide and t-butoxypotassium; and the acyloxylation is preferably exemplified by a reaction of the above-mentioned hydroxyl groups with an acid anhydride without resort to any solvent.

The term "antioxidant" as used herein involves mixtures of the 4-acylamino-2,2,6,6-tetramethylpiperidine derivatives, which are employed as the active ingredients, with appropriate diluents, solvents, carriers, etc. at an arbitrary mixing ratio as well as the piperidine derivatives per se employed alone.

The antioxidants according to the present invention may comprise either one of the compounds represented by the formula (A) or a mixture of two or more of the same. The antioxidants may also contain publicly known deterioration inhibitors and fading inhibitors. Examples of the publicly known deterioration inhibitors and fading inhibitors usable together with the compounds of the present invention include hydroquinones, chromans, alkylphenols, alkoxyphenols, alkoxybensenes, anilines, indans, etc.

The antioxidants of the present invention are useful as, for example, fading inhibitors for color diffusion transfer photographic materials and antioxidants for inkjet colorants (dyes) The compounds of the present invention can be added to any of photosensitive materials, dye fixing materials (image receptor materials) and processing compositions.

To further illustrate the present invention in greater detail, and not by way of limitation, the following Examples will be given.

EXAMPLE 1

Synthesis of Inventive Compound (2) Illustrated

To 30.9 g of 4-amino-2,2,6,6-tetramethylpiperidine were added 45 ml of methanol and 34.2 g of D-(+)-glucono-1,5-lactone and the resultant mixture was heated under reflux for 2 hours. After cooling to 50° C., 200 ml of acetone was added thereto. Next, it was cooled to 20° C. and the crystals thus precipitated were taken up by filtration and washed with 70 ml of acetone, thus giving white crystals.

The compound thus obtained was identified as the illustrated compound (2) by mass spectrometry, NMR spectrometry and infrared absorption spectrometry.

Yield: 58.6 g (91.3%). Melting point: 160 to 161° C.

EXAMPLE 2

Synthesis of Inventive Compound (3) Illustrated

To 47.4 g of 4-amino-2,2,6,6-tetramethylpiperidine were added 21 ml of sulfolane and 38.4 g of DL-pantoyllactone and the resultant mixture was stirred at 105 to 110° C. for 4 hours. After cooling to 90° C., 150 ml of acetone was added thereto. Next, it was cooled to 20° C. and the crystals thus precipitated were taken up by filtration and washed with 200 ml of acetone, thus giving white crystals.

The compound thus obtained was identified as the illustrated compound (3) by mass spectrometry, NMR spectrometry and infrared absorption spectrometry.

Yield: 66.6 g (78.7%). Melting point: 168 to 170° C.

EXAMPLE 3

First, a method for producing a dye fixing element will be illustrated.

A method for preparing a dispersion of a fluorescent brightener and a stainproofing agent will be described.

25 g of a fluorescent brightener (1), 32 g of a stainproofing agent (1) and 10 g of an anionic surfactant (2) were dissolved in 690 g of a high-boiling organic solvent (1) and 250 ml of ethyl acetate. The resultant solution was added to 1200 ml of a 25% aqueous solution of gelatin and dispersed in a homogenizer at 1250 rpm for 20 minutes. Next, 300 ml of water was further added thereto and the resultant mixture was stirred to give a uniform dispersion.

Next, a method for preparing a latex dispersion will be described.

20 g of gelatin and 30 g of a water-soluble polymer (3) were dissolved in 200 ml of water at 50° C. After cooling to 40° C., 117 g of a latex dispersion (1) was added thereto followed by stirring. In the dissolved state, the mixture was filtered through a 30 µm filter to give a uniform dispersion.

A dye fixing element R101 of the constitution shown in Table 1 was produced.

Water-soluble polymer (1) Sumika Gel L5-H (manufactured by Sumitomo Chemical Co., Ltd.).

Water-soluble polymer (2) κ-carrageenan (manufactured by Taito Co., Ltd.).

Water-soluble polymer (3) dextran (Mw. 70,000).

Anionic surfactant (1)

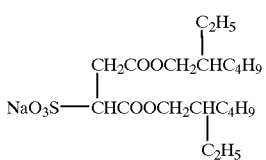

Anionic surfactant (2)

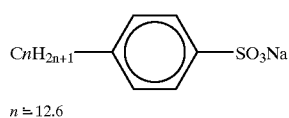

n ≒ 12.6

Anionic surfactant (3)

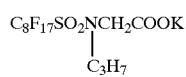

Ampholytic surfactant (4)

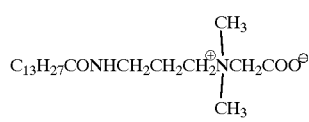

High-boiling solvent (1)

$C_{26}H_{46.9}Cl_{7.1}$

Empara 40 (manufactured by Ajinomoto Co., Ltd.)

Fluorescent brightener (1)

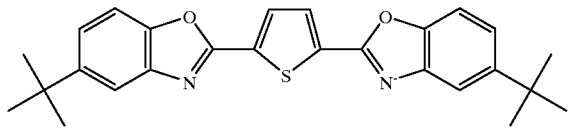

Stainproofing agent (1)

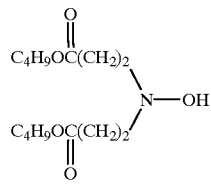

Mordant (1)

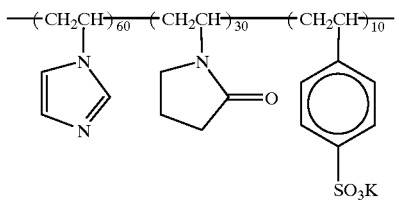

Hardening agent (1)

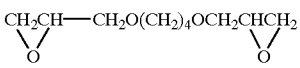

Latex dispersion (1)

Nipol LX814 (manufactured by Nippon Zeon Co., Ltd.)

Matting agent (1)

SYLOID 79 (manufactured by Fuji Davison Chemical Co., Ltd.)

TABLE 1

Constitution of dye fixing element R101

| Layer no. | Additive | Coating weight (mg/m²) |
|---|---|---|
| 4th layer | Water-soluble polymer (1) | 200 |
| | Water-soluble polymer (2) | 60 |
| | Potassium nitrate | 30 |
| | Anionic surfactant (1) | 8 |
| | Anionic surfactant (2) | 7 |
| | Matting agent (1) | 10 |
| 3rd layer | Gelatin | 250 |
| | Water-soluble polymer (1) | 30 |
| | Ampholytic surfactant (4) | 27 |
| | Hardening agent (1) | 190 |
| 2nd layer | Gelatin | 1400 |
| | Water-soluble polymer (1) | 130 |
| | Water-soluble polymer (3) | 660 |
| | Latex dispersion (1) | 1180 |
| | High-boiling solvent (1) | 690 |
| | Fluorescent brightener (1) | 25 |
| | Mordant (1) | 2350 |
| | Anionic surfactant (2) | 10 |
| | Guanidine picolinate | 2900 |
| | Stainproofing agent (1) | 32 |
| 1st layer | Gelatin | 190 |

TABLE 1-continued

Constitution of dye fixing element R101

| Layer no. | Additive | Coating weight (mg/m²) |
|---|---|---|
| | Water-soluble polymer (1) | 10 |
| | Anionic surfactant (1) | 10 |
| | Ampholytic surfactant (4) | 27 |
| | Hardening agent (1) | 190 |
| Support (1) polyethylene-laminated paper support (thickness: 206 μm) | | |

Coating weight of latex dispersion (1) means the weight of solid matters in latex dispersion.

TABLE 2

Support (1)

| Layer name | Composition | Film thickness (μm) |
|---|---|---|
| Surface PE layer | Gelatin | 0.1 |
| Surface PE layer (glossy) | Low-density polyethylene (density 0.923) : 89.2 parts surface-treated titanium oxide: 10.0 parts Marine blue : 0.8 parts | 35.0 |
| pulp layer | Woodfree paper (LBKR/NBKP = 1/1; density 1.080) | 140.8 |
| back PE layer (mat) | High-density polyethylene (density 0.960) | 30.0 |
| Back undercoat layer | Gelatin Colloidal silica | 0.05 0.05 |
| | | 206.0 |

Dye fixing elements R102 to R107 were produced in the same manner as in the dye fixing element R101 except for adding an antioxidant shown in Table A to the second layer.

These dye fixing elements were each combined with a photosensitive element PICTRO STAT 200 PS DONOR PS-DS marketed from Fuji Photo Film Co., Ltd. and a test image was obtained by using a color copy machine PICTRO STAT 200 marketed by the same company.

Namely, a full-colored original image was subjected to scanning exposure through a slit. The thus exposed photosensitive element was immersed in water maintained at 40° C. for 2.5 seconds and then squeezed with a roller followed by overlapping in such a manner that the dye fixing element came into contact with the film surface. After heating for 17 seconds by using a heat drum the temperature of which had been regulated to give a surface temperature of the water-absorbing film to 80° C., the photosensitive element was stripped from the dye fixing element, thus giving a vivid color image corresponding to the original image on the dye fixing element. Comparative compound (a):

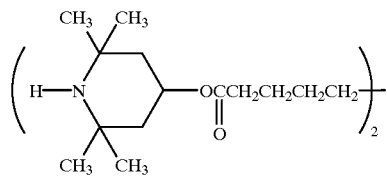

Color images thus formed by using the samples R101 to R107 were each provided with an ultraviolet absorption filter (manufactured by Fuji Photo Film Co., Ltd.) capable of cutting out rays of 400 nm and below and then irradiated with a xenon test (illuminance: 200,000 lx) for 8 days.

Evaluation was made based on the residual dye density ratio at the initial cyan density (a density in a gray part) of 2.0 of each sample.

In the measurement, use was made of a Fuji auto-recording density meter. Table A shows the obtained data.

TABLE A

| Dye Fixing element | Antioxidant | Addition level (g/m²) | Residual dye density ratio (%) | Note |
|---|---|---|---|---|
| R101 | — | — | 78 | comp. example |
| R102 | Comp: Compound a | 4 | 77 | do. |
| R103 | Compound (2) | 2 | 93 | invention |
| R104 | Do. (3) | 2 | 92 | do. |
| R105 | Do. (8) | 0.5 | 89 | do. |
| R106 | Do. (10) | 0.8 | 88 | do. |
| R107 | Do. (11) | 1.5 | 87 | do. |

As Table A shows, the compounds of the present invention have highly excellent antioxidant propert ies (fading inhibitory effects).

EXAMPLE 4

The following composition was prepared by using IIR (manufactured by POLYCER, butyl #100, degree of unstaturation 0.7%) as a resin base.

| | |
|---|---|
| POLYCER butyl #100 | 100 parts by weight |
| hard clay | 120 parts by weight |
| zinc white | 5 parts by weight |
| stearic acid | 2 parts by weight |
| sulfur | 1 part by weight |
| tetramethylthiuram disulfide | 2 parts by weight |
| SRF carbon | 10 parts by weight |
| mercaptobenzothiazole | 0.5 parts by weight. |

The composition was kneaded with a roll and then press-cured at 160° C. for 45 minutes to give a sheet of 2 mm in thickness. Next, this sheet was die-cut with a JIS No. 3 dumbbell to give a sample a. Also, samples b, c, d and e respectively containing 5 parts by weight of the compounds of the present invention (2), (3), (8) and (10) were obtained in the same manner. These samples were each placed in a gear oven at 120° C. for 100 hours and then the tensile strength (kg/mm²) and elongation (%) were measured. As a result, the samples with the use of the compounds of the present invention showed the antioxidant effects of the present invention.

The 4-acylamino-2,2,6,6-tetramethylpiperidine derivatives according to the present invention are useful as antioxidants.

While the invention has been described in detail and with reference to specific embodiments thereof, it will be apparent to one skilled in the art that various changes and modifications can be made therein without departing from the spirit and scope thereof.

What is claimed is:

1. 4-Acylamino-2,2,6,6-tetramethylpiperidine derivatives represented by formula (A'):

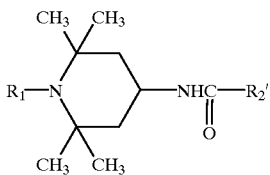

(A')

wherein $R_1$ represents a hydrogen atom, a hydroxyl group, an oxyradical group, an aliphatic group, an acyl group, an aliphatic oxy group or an acyloxy group; and $R_2'$ represents an alkyl group or an alkenyl group having 3 to 7 carbon atoms and 2 to 6 hydroxyl groups, said alkyl or alkenyl group being unsubstituted or substituted with an alkyl group.

2. An antioxidant composition comprising the 4-acylamino-2,2,6,6-tetramethylpiperidine derivative represented by formula (A):

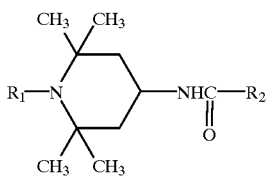

(A)

wherein $R_1$ represents a hydrogen atom, a hydroxyl group, an oxyradical group, an aliphatic group, an acyl group, an aliphatic oxy group or an acyloxy group; and $R_2$ represents an aliphatic group having 3 to 7 carbon atoms and two to six hydroxyl groups.

3. An antioxidant composition for color diffusion transfer photographic materials or inkjet dyes comprising the 4-acylamino-2,2,6,6-tetramethylpiperidine derivatives represented by the formula (A) as defined in claim 2.

4. The antioxidant composition of claim 2 further comprising diluent, solvents and carriers.

5. The antioxidant composition of claim 3 further comprising diluents, solvents and carriers.

6. The antioxidant composition of claim 4 further comprising deterioration inhibitors and fading inhibitors selected from the group consisting of hydroquinones, chromans, alkylphenols, alkoxyphenols, alkoxybenzenes, anilines and indans.

7. The antioxidant composition of claim 5 further comprising deterioration inhibitors and fading inhibitors selected from the group consisting of hydroquinones, chromans, alkylphenols, alkoxyphenols, alkoxybenzenes, anilines and indans.

8. The 4-Acylamino-2,2,6,6-tetramethylpiperidine derivative of claim 1 wherein said aliphatic group represented by $R_1$ is selected from the group consisting of alkyl and alkenyl.

9. The 4-Acylamino-2,2,6,6-tetramethylpiperidine derivative of claim 1 wherein said acyl group represented by $R_1$ is selected from the group consisting of alkylcarbonylamino, alkenylcarbonylamino and arylcarbonylamino.

10. The 4-Acylamino-2,2,6,6-tetramethylpiperidine derivative of claim 1 wherein said aliphatic oxy group represented by $R_1$ is selected from the group consisting of alkoxy and alkenoxy.

11. The 4-Acylamino-2,2,6,6-tetramethylpiperidine derivative of claim 1 wherein said acyloxy group represented by $R_1$ is selected from the group consisting of alkylcarbonyloxy, alkenylcarbonyloxy and arylcarbonyloxy.

12. The antioxidant composition according to claim 2 wherein said aliphatic group represented by $R_1$ is selected from the group consisting of alkyl and alkenyl.

13. The antioxidant composition according to claim 2 wherein said acyl group represented by $R_1$ is selected from the group consisting of alkylcarbonylamino, alkenylcarbonylamino and arylcarbonylamino.

14. The antioxidant composition according to claim 2 wherein said aliphatic oxy group represented by $R_1$ is selected from the group consisting of alkoxy and alkenoxy.

15. The antioxidant composition according to claim 2 wherein said acyloxy group represented by $R_1$ is selected from the group consisting of alkylcarbonyloxy, alkenylcarbonyloxy and arylcarbonyloxy.

16. The antioxidant composition according to claim 2 wherein said aliphatic group represented by $R_2$ is alkyl or alkenyl.

17. The antioxidant composition according to claim 2 wherein said aliphatic group represented by $R_2$ is alkyl or alkenyl substituted with alkyl.

18. The antioxidant composition according to claim 2 wherein $R_2$ is selected from the group consisting of 1,3-dihydroxy-2,2-dimethylpropyl and 1,2,3,4,5-pentahydroxypentyl.

* * * * *